(12) United States Patent
Holloway et al.

(10) Patent No.: US 6,521,248 B1
(45) Date of Patent: Feb. 18, 2003

(54) MICRO-CLUSTER LIQUIDS AND METHODS OF MAKING AND USING THEM

(75) Inventors: Michael A. Holloway, Humble, TX (US); William D. Holloway, Jr., San Diego, CA (US)

(73) Assignee: Bio-Hydration Research Lab, Inc., San Diego, CA (US)

( * ) Notice: Subject to any disclaimer, the term of this patent is extended or adjusted under 35 U.S.C. 154(b) by 16 days.

(21) Appl. No.: 09/698,537

(22) Filed: Oct. 26, 2000

Related U.S. Application Data
(60) Provisional application No. 60/161,546, filed on Oct. 26, 1999.

(51) Int. Cl.$^7$ .......................... A61K 47/00; A61K 9/00; C02F 3/00
(52) U.S. Cl. ........................ 424/439; 424/400; 210/615
(58) Field of Search ................................ 424/439, 400; 210/615

(56) References Cited

U.S. PATENT DOCUMENTS

| | | | | |
|---|---|---|---|---|
| 4,261,521 A | | 4/1981 | Ashbrook | 241/5 |
| 4,764,283 A | | 8/1988 | Ashbrook et al. | 210/695 |
| 4,957,626 A | | 9/1990 | Ashbrook et al. | 210/695 |
| 5,236,722 A | | 8/1993 | Schroeder | 426/67 |
| 5,318,702 A | | 6/1994 | Ashbrook | 210/188 |
| 5,435,913 A | | 7/1995 | Ashbrook | 210/188 |
| 5,711,950 A | * | 1/1998 | Lorenzen | 424/400 |
| 5,766,490 A | | 6/1998 | Taylor et al. | 210/758 |
| 5,814,222 A | * | 9/1998 | Zelenak et al. | 210/615 |
| 5,885,467 A | | 3/1999 | Zelenák et al. | 210/758 |

OTHER PUBLICATIONS

DWPI, ACC–No. 1993–316790, JP 05228476 (English abstract).*
Yang, Xiaolin et al., "Large Protonated Water Clusters $H^+(H_2O)_n$ ($1 \leq n > 60$): The Production and Reactivity of Clathrate–like Structures under Thermal Conditions," *J. Am. Chem. Soc.* 111: 6845–6846 (1989).
Weiller, B.H. et al., "The reactions of iron clusters with water," *J. Chem. Phys.* 91(8):4714–4727 (Oct. 15, 1989).
Putterman, Seth J., Sonoluminescence: Sound into Light, *Scientific American* 46–51 (Feb. 1995).
VRTX Technology, "Water Stabilization Schematic," www.vrtx–technologies.com/HowVRTXworks/?VRTX= Diagram (Dec. 20, 2001).
Weninger, K.R. et al., "Energy Focusing in a Converging Fluid Flow: Implications for Sonoluminescence," *Physical Review Letters* 83, 10: 2081–2084 (Sep. 6, 1999).*

* cited by examiner

Primary Examiner—Thurman K. Page
Assistant Examiner—Blessing Fubara
(74) *Attorney, Agent, or Firm*—Darby & Darby

(57) ABSTRACT

The invention provides novel micro-cluster liquids and methods for manufacturing and using them. The micro-cluster liquids comprise fractionized or micro-cluster liquids, (e.g. water, such as oxygenated micro-cluster water). The methods comprise causing cavitation of a liquid to form cavitation bubbles under a first pressure followed by depressurization to a second pressure to cause implosion and explosion of the cavitation bubbles such that acoustical energy shockwaves are created. The micro-cluster water (e.g., oxygenated micro-cluster water) is used to deliver hydration, oxygenation, or agents, such as nutritional agents or medications, and increasing overall cellular performance and exchanging liquids in the cell within minutes of consumption.

53 Claims, 8 Drawing Sheets

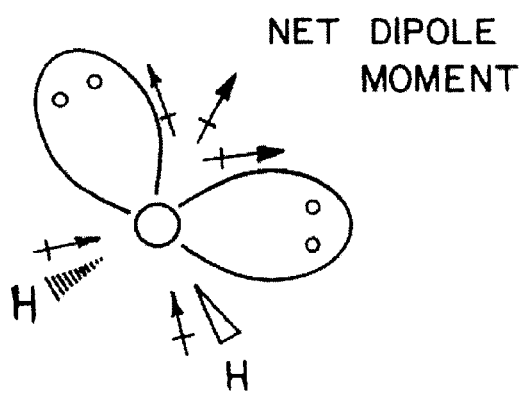
FIG. 1
FIG. 2
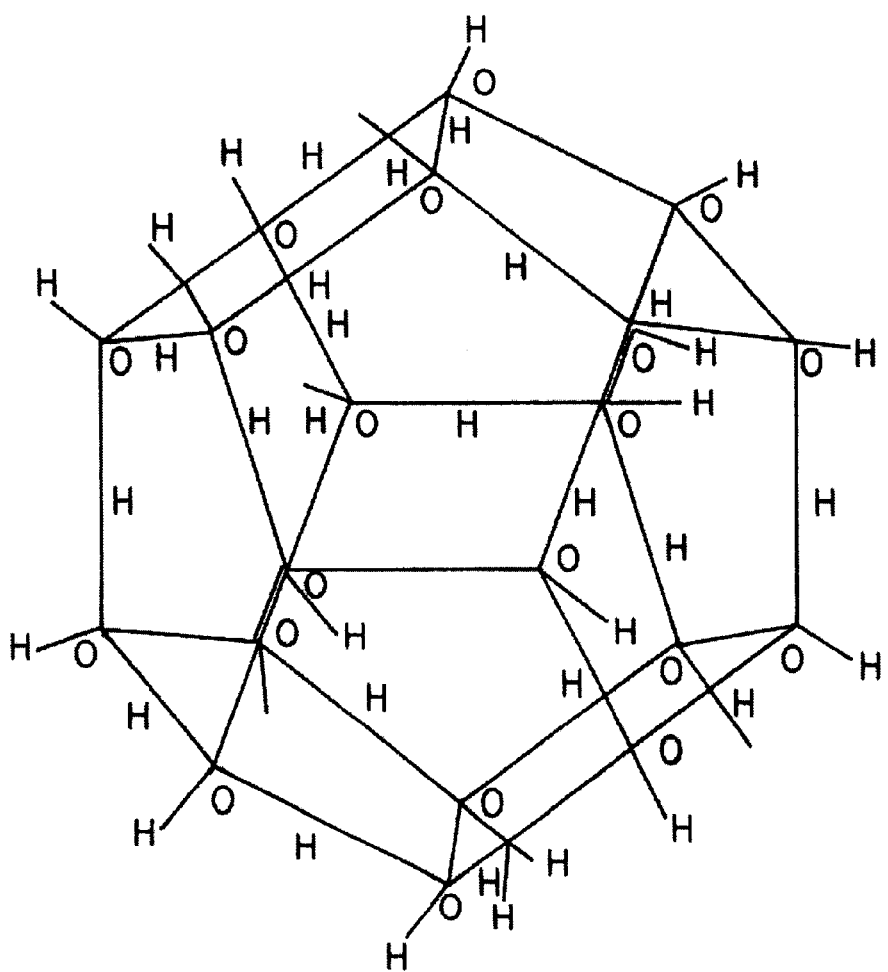

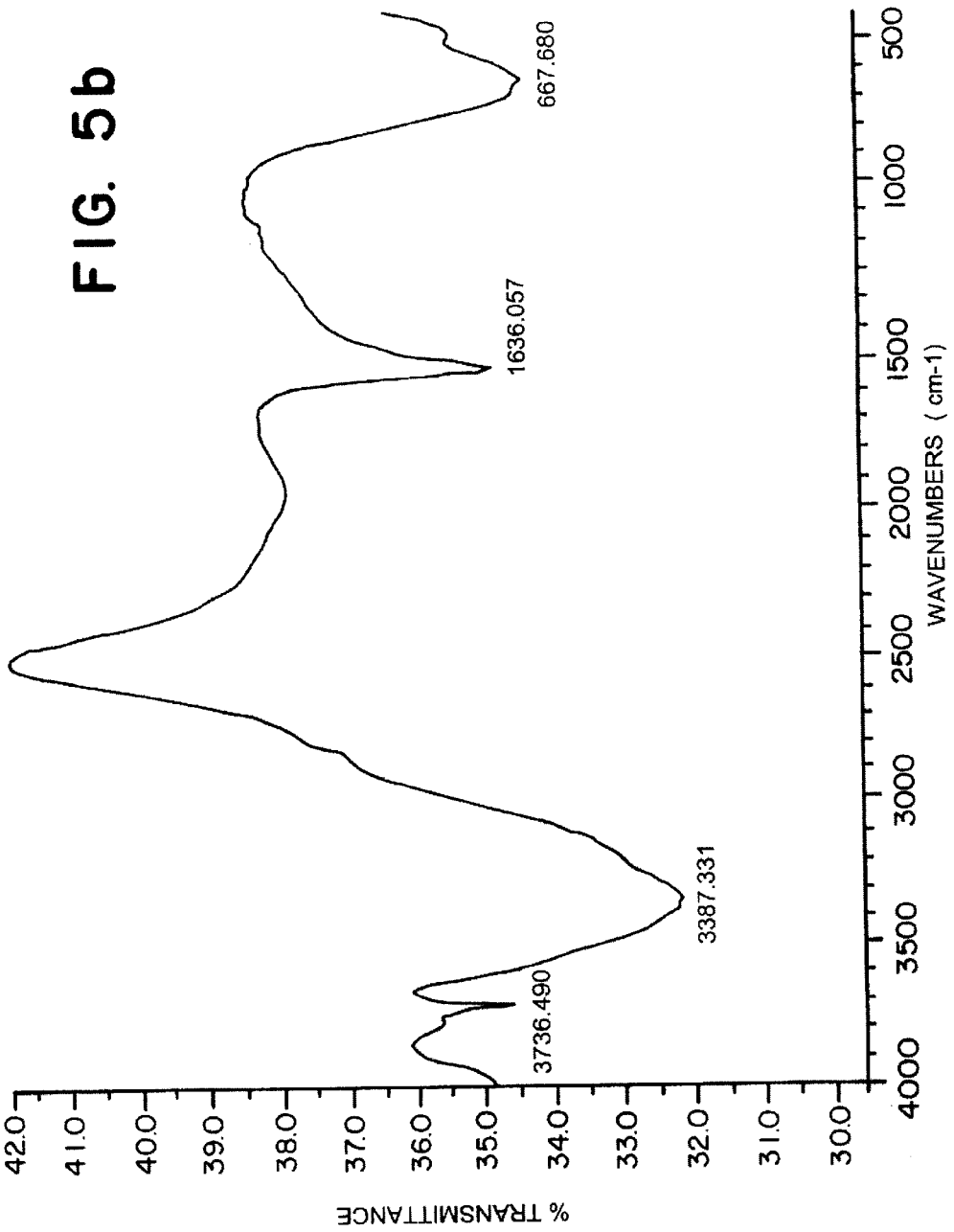

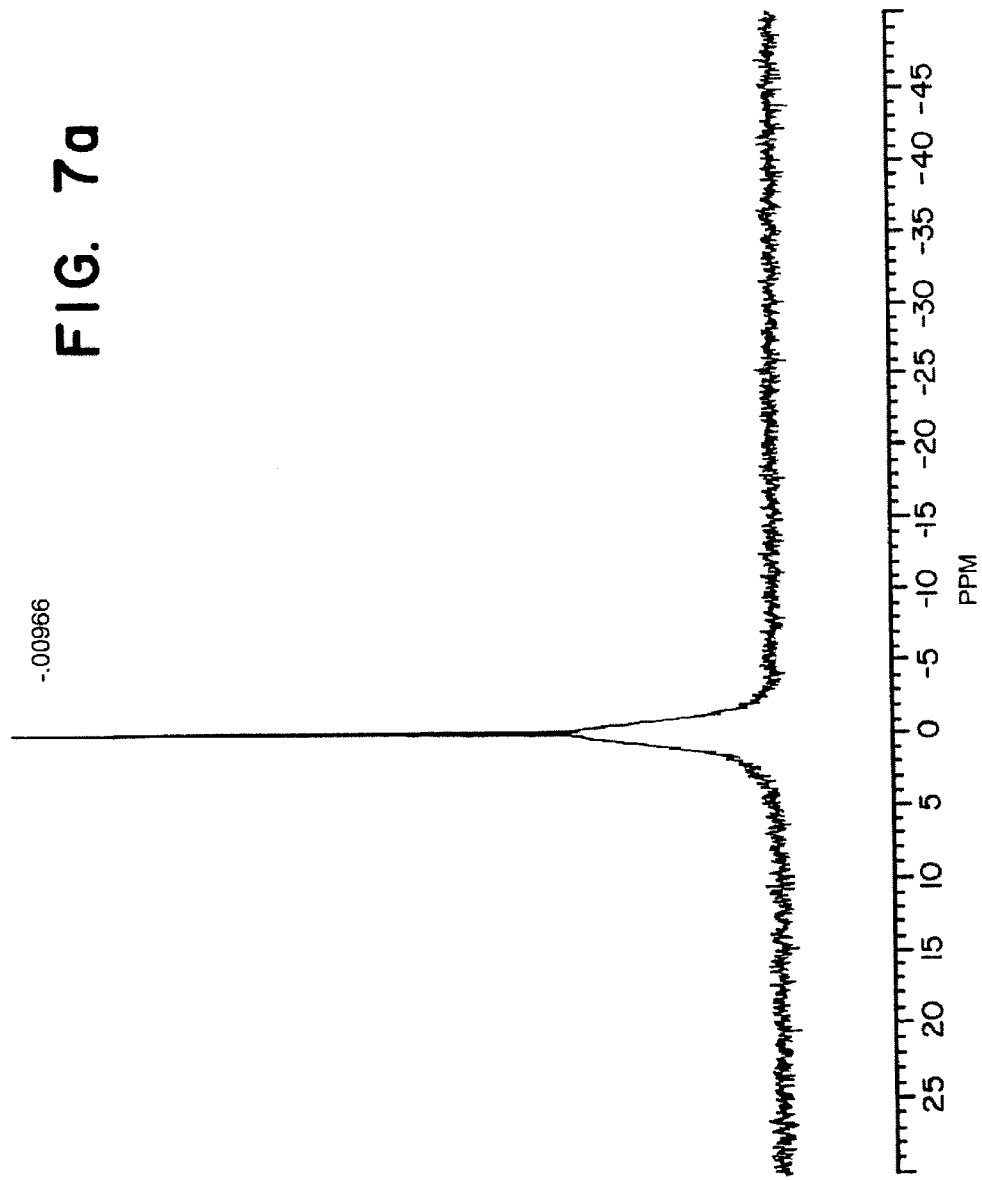

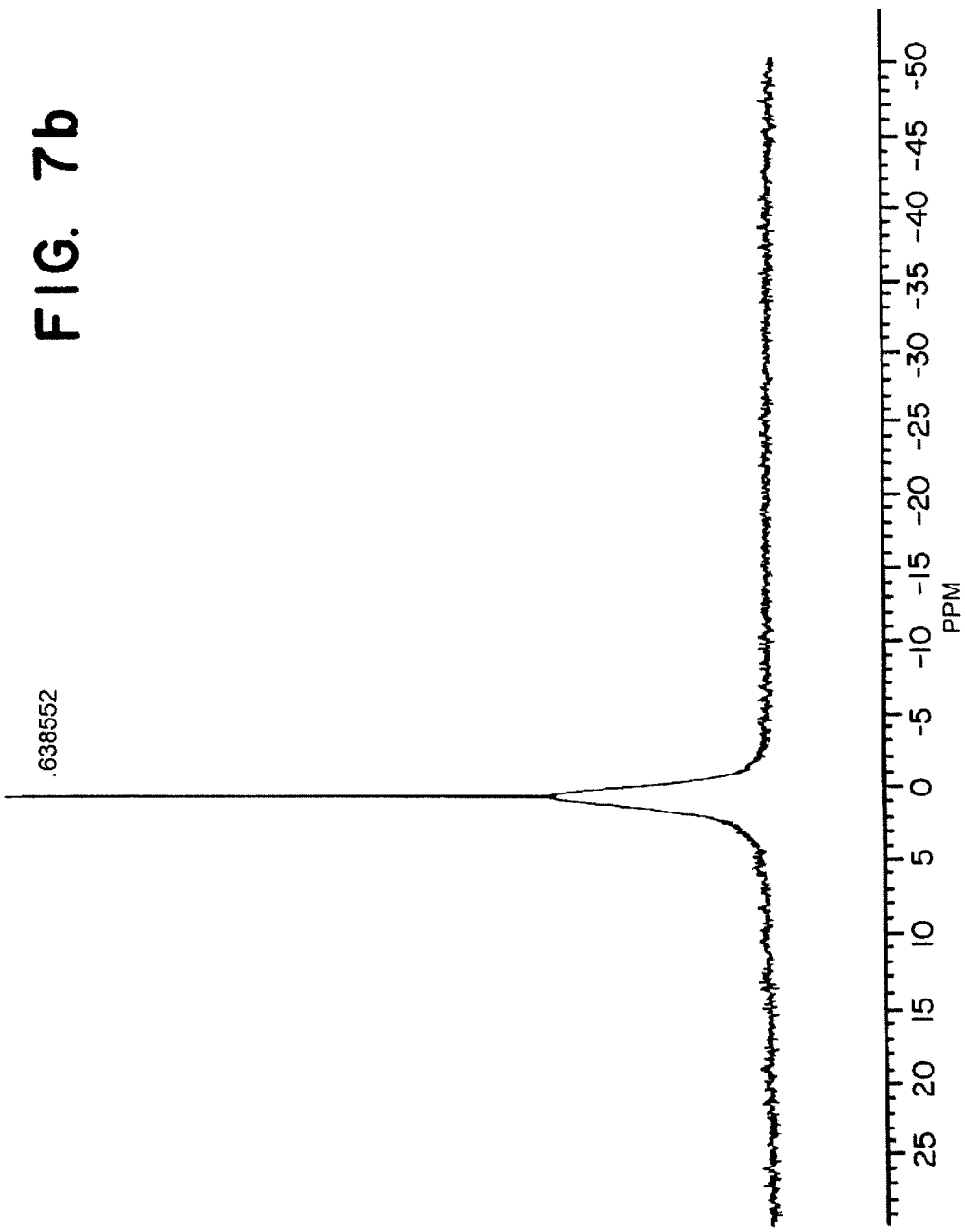

MICRO-CLUSTER LIQUIDS AND METHODS OF MAKING AND USING THEM

RELATED APPLICATIONS

Under 35 USC §119(e)(1), this application claims the benefit of priority of prior U.S. provisional application 60/161,546, filed Oct. 26, 1999. This aforementioned application is explicitly incorporated herein by reference in its entirety and for all purposes.

FIELD OF THE INVENTION

The invention relates generally to micro-cluster liquids and methods of making and using them. The present invention provides a process of making micro-cluster liquid and methods of use thereof.

BACKGROUND OF THE INVENTION

Water is composed of individual $H_2O$ molecules that may bond with each other through hydrogen bonding to form clusters that have been characterized as five species: unbonded molecules, tetrahedral hydrogen bonded molecules comprised of five (5) $H_2O$ molecules in a quasi-tetrahedral arrangement and surface connected molecules connected to the clusters by 1,2 or 3 hydrogen bonds, (U.S. Pat. No. 5,711,950 Lorenzen; Lee H.). These clusters can then form larger arrays consisting of varying amounts of these micro-cluster molecules with weak long distance van der Waals attraction forces holding the arrays together by one or more of such forces as; (1) dipole-dipole interaction, i.e., electrostatic attraction between two molecules with permanent dipole moments; (2) dipole-induced dipole interactions in which the dipole of one molecule polarizes a neighboring molecule; and (3) dispersion forces arising because of small instantaneous dipoles in atoms. Under normal conditions the tetrahedral micro-clusters are unstable and reform into larger arrays from agitation, which impart London Forces to overcome the van der Waals repulsion forces. Dispersive forces arise from the relative position and motion of two water molecules when these molecules approach one another and results in a distortion of their individual envelopes of intra-atomic molecular orbital configurations. Each molecule resists this distortion resulting in an increased force opposing the continued distortion, until a point of proximity is reached where London Inductive Forces come into effect. If the velocities of these molecules are sufficiently high enough to allow them to approach one another at a distance equal to van der Waals radii, the water molecules combine.

There is currently a need for a process whereby large molecular arrays of liquids can be advantageously fractionated. Furthermore, there is a desire for smaller molecular (e.g., micro-clusters) of water for consumption, medicinal and chemical processes.

SUMMARY OF THE INVENTION

The inventors have discovered that liquids, which form large molecular arrays, such as through various electrostatic and van der Waal forces (e.g., water), can be disrupted through cavitation into fractionated or micro-cluster molecules (e.g., theoretical tetrahedral micro-clusters of water). The inventors have further discovered a method for stabilizing newly created micro-clusters of water by utilizing van der Waals repulsion forces. The method involves cooling the micro-cluster water to a desired density, wherein the micro-cluster water may then be oxygenated. The micro-cluster water is bottled while still cold. In addition, by overfilling the bottle and capping while the micro-cluster oxygenated water is dense (i.e., cold), the London forces are slowed down by reducing the agitation which might occur in a partially filled bottle while providing a partial pressure to the dissolved gases (e.g., oxygen) in solution thereby stabilizing the micro-clusters for about 6 to 9 months when stored at 40 to 70 degrees Fahrenheit.

The present invention provides a process for producing a micro-cluster liquid, such as water, comprising subjecting a liquid to cavitation such that dissolved entrained gases in the liquid form a plurality of cavitation bubbles; and subjecting the liquid containing the plurality of cavitation bubbles to a reduced pressure, wherein the reduction in pressure causes breakage of large liquid molecule matrices into smaller liquid molecule matrices. In another embodiment the liquid is substantially free of minerals and can be water which may also be substantially free of minerals. The embodiment provides for a process which is repeated until the water reaches about 140° C. (about 60° C.). The cavitation can be provided by subjecting the liquid to a first pressure followed by a rapid depressurization to a second pressure to form cavitation bubbles. The pressurization can be provided by a pump. In one embodiment the first pressure is about 55 psig to more than 120 psig. In another embodiment the second pressure is about atmospheric pressure. The embodiment can be carried out such that the pressure change caused the plurality of cavitation bubbles to implode or explode. The pressure change may be performed to create a plasma which dissociates the local atoms and reforms the atom at a different bond angle and strength. In another embodiment the liquid is cooled to about 4° C. to 15° C. Further embodiment comprises providing gas to the micro-cluster liquid, such as where the gas is oxygen. In a further embodiment the oxygen is provided for about 5 to about 15 minutes.

In a further embodiment, the invention provides a process for producing a micro-cluster liquid, comprising subjecting a liquid to a pressure sufficient to pressurize the liquid; emitting the pressurized liquid such that a continuous stream of liquid is created; subjecting the continuous stream of liquid to a multiple rotational vortex having a partial vacuum pressure such that dissolved and entrained gases in the liquid form a plurality of cavitation bubbles; and subjecting the liquid containing the plurality of cavitation bubbles to a reduced pressure, wherein the plurality of cavitation bubbles implode or explode causing shockwaves that break large liquid molecule matrices into smaller liquid molecule matrices. In a further embodiment the liquid is substantially free of minerals and in an additional embodiment the liquid is water, preferably substantially free of minerals. The invention provides that the process can be repeated until the water reaches about 140° F. (about 60° C.). In another embodiment the cavitation is provided by subjecting the liquid to a first pressure followed by a rapid depressurization to a second pressure to form cavitation bubbles. Further the invention provides that the pressurization is provided by a pump. In a further embodiment the first pressure is about 55 psig to more than 120 psig and, in another embodiment the second pressure is about atmospheric pressure, including embodiments where the second pressure is less than 5 psig. The invention also provides for micro-cluster liquid where the pressure change causes the plurality of cavitation bubbles to implode or explode. In a further embodiment, the pressure change creates a plasma which dissociates the local atoms and reforms the atoms at a different bond angle and strength. The invention also provides a process where the liquid is cooled to about 4° C. to 15° C. In another embodiment, the invention provides subjecting a gas to the micro-cluster liquid. Preferably, the gas is oxygen, especially oxygen administered for about 5 to 15 minutes and more preferably at pressure from about 15 to 20 psig.

The present invention also provides for a composition comprising a micro-cluster water produced according to the procedures noted above.

Still another aspect of the invention is a micro-cluster water which has any or all of the properties of a conductivity of about 3.0 to 4.0 μmhos/cm, a FTIR spectrophotometric pattern with a major sharp feature at about 2650 wave numbers, a vapor pressure between about 40° C. and 70° C. as determined by thermogravimetric analysis, and an $^{17}O$ NMR peak shift of at least about +30 Hertz, preferably at least about +40 Hertz relative to reverse osmosis water.

The present invention further provides for the use of the micro-cluster water of the invention for such purposes as modulating cellular performance and lowering free radical levels in cells by contacting the cell with the micro-cluster water.

The present invention further provides a delivery system comprising a micro-cluster water (e.g., an oxygenated microcluster water) and an agent, such as a nutritional agent, a medication, and the like.

Further, the micro-cluster water of the invention can be used to remove stains from fabrics by contacting the fabric with the micro-cluster water.

The details of one or more embodiments of the invention are set forth in the accompanying drawings and the description below. Other features, objects, and advantages of the invention will be apparent from the description and drawings, and from the claims.

All publications, patents and patent applications cited herein are hereby expressly incorporated by reference for all purposes.

BRIEF DESCRIPTION OF THE DRAWINGS

FIG. 1 shows a water molecule and the resulting net dipole moment.

FIG. 2 shows a large array of water molecules.

DESCRIPTION OF THE PREFERRED EMBODIMENTS

Liquids, including for example, alcohols, water, fuels and combinations thereof, are comprised of atoms and molecules having complex molecular arrangements. Many of these arrangements result in the formation of large molecular arrays of covalently bonded atoms having non-covalent interactions with adjacent molecules, which in turn interact via additional non-covalent interactions with yet other molecules. These large arrays, although stable, are not ideal for many applications due to their size. Accordingly it is desirable to create and provide liquids having smaller arrays by reducing the number of non-covalent interactions. These smaller molecules are better able to penetrate and react in biological and chemical systems. In addition, the smaller molecular arrays provide novel characteristics that are desirable.

As used herein, "covalent bonds" means bonds that result when atoms share electrons. The term "non-covalent bonds" or "non-covalent interactions" means bonds or interactions wherein electrons are not shared between atoms. Such non-covalent interactions include, for example, ionic (or electrovalent) bonds, formed by the transfer of one or more electrons from one atom to another to create ions, interactions resulting from dipole moments, hydrogen bonding, and van der Waals forces. Van der Waals forces are weak forces that act between non-polar molecules or between parts of the same molecule, thus bringing two groups together due to a temporary unsymmetrical distribution of electrons in one group, which induces an opposite polarity in the other. When the groups are brought closer than their van der Waals radii, the force between them becomes repulsive because their electron clouds begin to interpenetrate each other.

Figure 3:
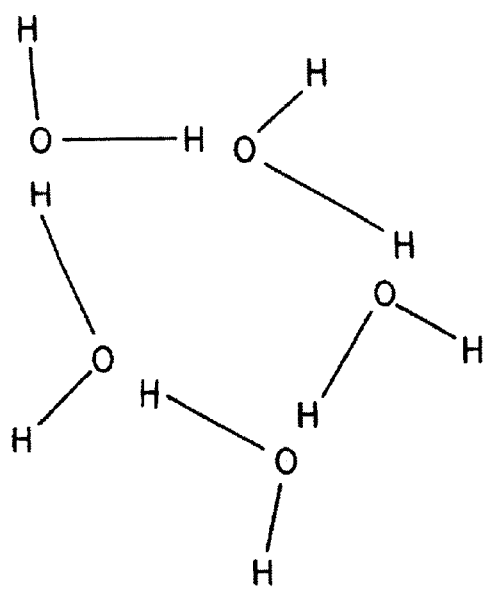
FIG. 3 shows a micro-cluster of water having 5 water molecules forming a tetrahedral shape.

Numerous liquids are applicable to the techniques described herein. Such liquids include water, alcohols, petroleum and fuels. Liquids, such as water, are molecules comprising one or more basic elements or atoms (e.g., hydrogen and oxygen). The interaction of the atoms through covalent bonds and molecular charges form molecules. A molecule of water has an angular or bent geometry. The H—O—H bond angle in a molecule of water is about 104.5° to 105°. The net dipole moment of a molecule of water is depicted in FIG. 1. This dipole moment creates electrostatic forces that allow for the attraction of other molecules of water. Recent studies by Pugliano et al., (Science, 257:1937, 1992) have suggested the relationship and complex interactions of water molecules. These studies have revealed that hydrogen bonding and oxygen-oxygen interactions play a major role in creating large clusters of water molecules. Substantially purified water forms complex structures comprising multiple water molecules each interacting with an adjacent water molecule (as depicted in FIG. 2) to form large arrays. These large arrays are formed based upon, for example, non-covalent interactions such as hydrogen bond formation and as a result of the dipole moment of the molecule. Although highly stable, these large molecules have been suggested to be detrimental in various chemical and biological reactions. Accordingly, in one embodiment, the present invention provides a method of forming fractionized or micro-cluster water as depicted in FIG. 3 having as few as about 5 molecules of water.

The present invention provides small micro-cluster liquids (e.g., micro-cluster water molecules) a method for manufacturing fractionized or micro-cluster water and methods of use in the treatment of various biological conditions.

Accordingly, the present invention provides a method for manufacturing fractionized or micro-cluster liquids (e.g., water) comprising pressurizing a starting liquid to a first pressure followed by rapid depressurization to a second pressure to create a partial vacuum pressure that results in release of entrained gases and the formation of cavitation bubbles. The thermo-physical reactions provided by the implosion and explosion of the cavitation bubbles results in an increase in heat and the breaking of non-covalent interactions holding large liquid arrays together. This process can be repeated until a desired physical-chemical trait of the fractionized liquid is obtained. Where the liquid is water, the process is repeated until the water temperature reaches about 140° F. (about 60° C.). The resulting smaller or fractionized liquid is cooled under conditions that prevent reformation of the large arrays. As used herein, "water" or "a starting water" includes tap water, natural mineral water, and processed water such as purified water.

Any number of techniques known to those of skill in the art can be used to create cavitation in a liquid so long as the cavitating source is suitable to generate sufficient energy to break the large arrays. The acoustical energy produced by the cavitation provides energy to break the large liquid arrays into smaller liquid clusters. For example, the use of acoustical transducers may be utilized to provide the required cavitation source. In addition, cavitation can be induced by forcing the liquid through a tube having a constriction in its length to generate a high pressure before the constriction, which is rapidly depressurized following the constriction. Another example, includes forcing a liquid through a pump in reverse direction through a rotational volute.

In one embodiment, a liquid to be fractionized is pressurized into a rotational volute to create a vortex that reaches partial vacuum pressures releasing entrained gases as cavitation bubbles when the rotational vortex exits through a tapered nozzle at or close to atmospheric pressure. This sudden pressurization and decompression causes implosion and explosion of cavitation bubbles that create acoustical energy shockwaves. These shockwaves break the covalent and non-covalent bonds on the large liquid arrays, break the weak array bonds, and form micro-cluster or fractionized liquid consisting of, for example, about five (5) $H_2O$ molecules in a quasi tetrahedral arrangement (as depicted in FIG. 3), and impart an electron charge to the micro-cluster liquid thus producing electrolyte properties in the liquid. The micro-cluster liquid is recycled until desired number of micro-cluster liquid molecules are formed to reach a given surface tension and electron charge, as determined by the temperature rise of the liquid over time as cavitation bubbles impart kinetic heat to the processed liquid. Once the desired surface tension and electron charge are reached the micro-cluster liquid is cooled until liquid density increases. The desired surface tension and electron charge can be measured in any number of ways, but is preferably detected by temperature. Once the liquid reaches a desired density, typically at about 4 to 15° C., a gas, such as, for example, molecular oxygen, can be introduced for a sufficient amount of time to attain the desired quantity of oxygen in the micro-cluster liquid. The micro-cluster liquid is then aliquoted into a container or bottle, preferably filled to maximum capacity, and capped while the gassed micro-cluster liquid is still cool, so as to provide a partial pressure to the gassed micro-cluster liquid as the temperature reaches room temperature. This enables larger quantities of dissolved gas to be maintained in solution due to increased partial pressure on the bottles contents.

Figure 4:
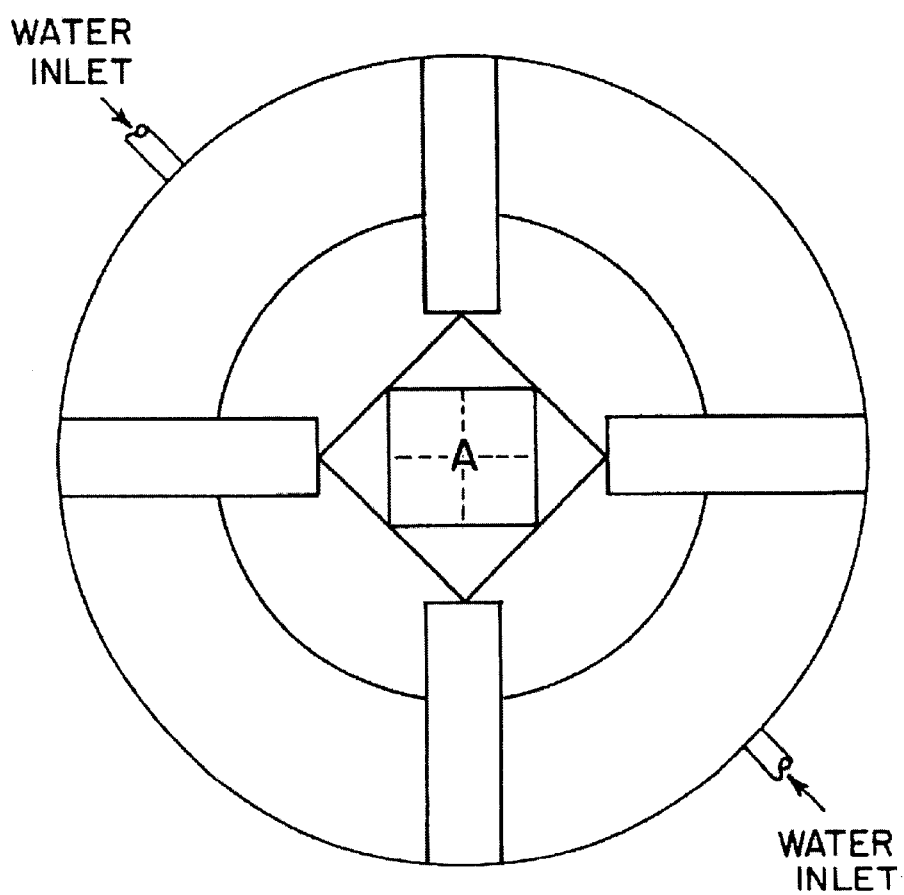
FIG. 4 shows an example of a device useful in creating cavitation in a liquid. The device provides inlets for a liquid, wherein the liquid is then subjected to multiple rotational vortexes reaching partial vacuum pressures of about 27" Hg. The liquid then exits the device at point A through an acceleration tube into a chamber less than the pressure within the device (e.g., about atmospheric pressure).

The present invention provides a method for making a micro-cluster or fractionized water or liquid, for ease of explanation water will be used as the liquid being described, however any type liquid may be substituted for water. A starting water such as, for example, purified or distilled water is preferably used as a base material since it is relatively free of mineral content. The water is then placed into a food grade stainless steel tank for processing. By subjecting the starting water to a pump capable of supplying a continuous pressure of between about 55 and 120 psig or higher a continuous stream of water is created. This stream of water is then applied to a suitable device (see for example FIG. 4) capable of establishing a multiple rotational vortex reaching partial vacuum pressures of about 27" Hg, thereby reaching the vapor pressure of dissolved entrained gases in the water. These gases form cavitation bubbles that travel down multiple acceleration tubes exiting into a common chamber at or close to atmospheric pressure. The resultant shock waves produced by the imploding and exploding cavitation bubbles breaks the large water arrays into smaller water molecules by repeated recirculation of the water. The recycling of the water creates increases results in an increase in temperature of the water. The heat produced by the imploding and exploding cavitation bubbles release energy as seen in sonoluminescence, in which the temperature of sonoluminance bubbles are estimated to range from 10 to 100 eV or 2,042.033 degrees Fahrenheit at 19,743,336 atmospheres. However the heat created is at a sub micron size and is rapidly absorbed by the surrounding water imparting its kinetic energy. The inventors have determined that the breaking of these large arrays into smaller water molecules can be manipulated through a sinusoidal wave utilizing cavitation, and by monitoring the rise in temperature one can adjust the osmotic pressure and surface tension of the water under treatment. The inventors have determined that the ideal temperature for oxygenated micro-cluster water (Penta-hydrate™) is about 140 degrees F. (about 60° C.). This can be accomplished by using four opposing vortex volutes with a 6-degree acceleration tube exiting into a common chamber at or close to atmospheric pressure, less than 5 pounds backpressure.

As mentioned above, the inventors have also discovered that liquids undergo a sinusoidal fluctuation in heat/temperature under the process described herein. Depending upon the desired physical-chemical traits, the process is repeated until a desired point in the sinusoidal curve is established at which point the liquid is collected and cooled under conditions to inhibit the formation of large molecular arrays. For example, and not by way of limitation, the inventors have discovered that water processed according to the methods described herein undergoes a sinusoidal heating process. During the production of this water a high negative charge is created and imparted to the water. Voltages of −350 mV to −1 volt have been measured with a superimposed sinusoidal wave with a frequency of 800 cycles or higher depending on operating pressures and subsequent water velocities. The inventors have found that the third sinusoidal peak in temperature provides an optimal number of micro-cluster structures for water. Although the inventors are under no duty to provide the mechanism or theory of action, it is believed that the high negative ion production serves as a ready source of donor electrons to act as antioxidants when consumed and further act to stabilize the water micro-clusters and help prevent reformation of the large arrays by aligning the water molecules exposed to the electrostatic field of the negative charge. While not wanting to be bound to a particular theory, it is believed that the high temperatures achieved during cavitation may form a plasma in the water which dissociates the $H_2O$ atoms and which then reform at a different bond association, as evidenced by the FTIR and NMR test data, to generate a different structure.

It will be recognized by those skilled in the art that the water of the present invention can be further modified in any number of ways. For example, following formation of the micro-cluster water, the water may be oxygenated as described herein, further purified, flavored, distilled, irradiated, or any number of further modifications known in the art and which will become apparent depending on the final use of the water.

In another embodiment, the present invention provides methods of modulating the cellular performance of a tissue or subject. The micro-cluster water (e.g., oxygenated microcluster water) can be designed as a delivery system to deliver hydration, oxygenation, nutrition, medications and increasing overall cellular performance and exchanging liquids in the cell and removing edema. Tests accomplished utilizing an RJL Systems Bio-Electrical Impedance Analyzer model BIA101Q Body Composition Analysis System™ demonstrated substantial intracellular and extracellular hydration changes in as little as 5 minutes. Tests were accomplished on a 58-year-old male 71.5" in height 269 lbs, obese body type. Baseline readings were taken with Bio-Electrical Impedance Analyzer™ as listed below.

As described in the Examples below it is contemplated that the micro-cluster water of the present invention provides beneficial effects upon consumption by a subject. The subject can be any mammal (e.g, equine, bovine, porcine, murine, feline, canine) and is preferably human. The dosage of the micro-cluster water or oxygenated micro-cluster water (Penta-hydrate™) will depend upon many factors recognized in the art, which are commonly modified and adjusted. Such factors include, age, weight, activity, dehydration, body fat, etc. Typically 0.5 liters of the oxygenated micro-cluster water of the invention provide beneficial results. In addition, it is contemplated that the micro-cluster water of the invention may be administered in any number of ways known in the art, including, for example, orally and intravenously alone or mixed with other agents, compounds and chemicals. It is also contemplated that the water of the invention may be useful to irrigate wounds or at the site of a surgical incision. The water of the invention can have use in the treatment of infections, for example, infections by anaerobic organisms may be beneficially treated with the micro-cluster water (e.g., oxygenated microcluster water).

In another embodiment, the micro-cluster water of the invention can be used to lower free radical levels and, thereby, inhibit free radical damage in cells.

In still another embodiment the micro-cluster water of the invention can be used to remove stains from fabrics, such as cotton.

The following examples are meant to illustrate but no limit the present invention. Equivalents of the following examples will be recognized by those skilled in the art and are encompassed by the present disclosure.

EXAMPLE 1

How to Make Micro-Cluster Water

Described below is one example of a method for making micro-cluster liquids. Those skilled in the art will recognize alternative equivalents that are encompassed by the present invention. Accordingly, the following examples is not to be construed to limit the present invention but are provided as an exemplary method for better understanding of the invention.

325 gallons of steam distilled water from Culligan Water or purified in 5 gallon bottles at a temperature about 29 degrees C. ambient temperature, was placed in a 316 stainless steel non-pressurized tank with a removable top for treatment. The tank was connected by bottom feed 2 ¼" 316 stainless steel pipe that is reduced to 1" NPT into a 20" U.S. filter housing containing a 5 micron fiber filter, the filter serves to remove any contaminants that may be in the water. Output of the 20" filter is connected to a Teel model 1V458 316 stainless steel Gear pump driven by a 3HP 1740 RPM 3 phase electric motor by direct drive. Output of the gear pump 1" NPT was directed to a cavitation device via 1" 316 stainless steel pipe fitted with a 1" stainless steel ball valve used for isolation only and past a pressure gauge. Output of the pump delivers a continuous pressure of 65 psig to the cavitation device.

The cavitation device was composed of four small inverted pump volutes made of Teflon without impellers, housed in a 316 stainless steel pipe housing that are tangentially fed by a common water source fed by the 1V458 Gear pump at 65 psig, through a ¼" hole that would normally be used as the discharge of a pump, but are utilized as the input for the purpose of establishing a rotational vortex. The water entering the four volutes is directed in a circle 360 degrees and discharged through what would normally be the suction side of a pump by the means of an 1" long acceleration tube with a ⅜" discharge hole, comprising what would normally be the suction side of a pump volute but in this case is utilized as the discharge side of the device. The four reverse fed volutes establish rotational vortexes that spin the water one 360 degree rotation and then discharge the water down the 5 degree decreasing angle from center line, acceleration tubes discharging the water into a common chamber at or close to atmospheric pressure. The common chamber was connected to a 1" stainless steel discharge line that fed back into the top of the 325-gallon tank containing the distilled water. At this point the water made one treatment trip through the device.

The process listed above is repeated continuously until the energy created by the implosions and explosions of the cavitation (e.g., due to the acoustical energy) have imparted its kinetic heat into the water and the water is at about 60 degrees Celsius.

Although the inventors are under no duty to explain the theory of the invention, the inventors provide the following theory in the way of explanation and are not to be bound by this theory. The inventors believe that the acoustical energy created by the cavitation brakes the static electric bonds holding a single tetrahedral Micro-Clusters of five $H_2O$ molecules together in larger arrays, thus decreasing their size and/or create a localized plasma in the water restructuring the normal bond angles into a different structure of water.

The temperature was detected by a hand held infrared thermal detector through a stainless stell thermo well. Other methods of assessing the temperature will be recognized by those of skill in the art. Once the temperature of 60 degrees C. has been reached the pump motor is secured and the water is left to cool. An 8 foot by 8 foot insulated room fitted with a 5,000 Btu. air conditioner is used to expedite cooling, but this is not required. It is important that the processed water not be agitated for cooling it should be moved as little as possible.

A cooling temperature of 4 degrees C. can be used, however 15 degrees C. is sufficient and will vary depending upon the quantity of water being cooled. Once sufficiently cooled to about 4 to 15 degrees C. the water can be oxygenated.

Once the water is cooled to desired temperature, the processed water is removed from the 325 gallon stainless steel tank into 5-gallon polycarbonate bottles for oxygenation.

Oxygenation is accomplished by applying gas $O_2$ at a pressure of 20 psig fed through a ¼" ID plastic line fitted with a plastic air diffuser utilized to make fine air bubbles (e.g., Lee's Catalog number 12522). The plastic tube is run through a screw on lid of the 5 gallon bottle until it reaches the bottom of the bottle. The line is fitted with the air diffuser at its discharge end. The Oxygen is applied at 20 psig flowing pressure to insure a good visual flow of oxygen bubbles. In one embodiment (Penta-hydrate™) the water is oxygenated for about five minutes and in another embodiment (Penta-hydrate Pro™) the water is oxygenated for about ten minutes.

Immediately after oxygenation the water is bottled in 500 ml PET bottles, filled to overflowing and capped with a pressure seal type plastic cap with inserted seal gasket. In one embodiment, the 0.5 L bottle is over filled so when the temperature of the water increases to room temperature it will self pressurize the bottle retaining a greater concentration of dissolved oxygen at partial pressure. This step not only keeps more oxygen in a dissolved state but also for preventing excessive agitation of the water during shipping.

EXAMPLE 2

The following are reports from individuals who used the water of the invention.

Elimination Of Edema:

Patient A: A 66-year-old Male presenting with (ALS) Amyothrophic Lateral Sclerosis (Lou Gherig's Disease) exhibited a shoulder hand syndrome with marked swelling of the left hand. This hand being the predominately affected limb. After consuming 500 ml of Penta-hydrate™ micro-cluster water the swelling of the left hand was dramatically reduced to normal state. Additional tests were accomplished over several weeks noting the same reduction of edema after consuming Penta-hydrate™ micro-cluster water. When Penta-hydrate™ was discontinued edema reoccurred overnight, upon consuming 500 ml of Penta-hydrate™ micro-cluster water edema was reduced within 4 to 6 hours.

Patient B: Is a 53 year old female with multijoint Acute Rheumatoid Arthritis of 6 year duration. She has been taking diuretics for dependent edema on a daily basis for 4 years. She began taking Penta-hydrate™ Micro-Cluster Water, 5 months ago in place of diuretics, consuming three (3) 500 ml bottles daily. Within one day the edema of the feet/legs and hands cleared. When Penta-hydrate™ was discontinued during a trip, the edema promptly returned. Upon resumption of Penta-hydrate™ Micro-Cluster Water the edema quickly cleared.

Increased Physical Endurance:

A 56-year-old woman diagnosed with "severe emphysema" and retired on full disability underwent experimental lung reduction surgery in December 1998 at St Elizabeth's Hospital in Boston. Each of the lungs upper lobes were removed and re-sectioned. While the surgery was deemed successful the patient had begun to deteriorate. The depression and loss of stamina was overcome by Oxy-Hi-drate Pro™. A 2 ⅓ increase in endurance is usually seen in response to subject taking Penta-hydrate™ and is caused by increased delivery of hydration to the cells, which is the delivery system for increased oxygenation and cellular energy production. Tests on numerous test subjects show marked increase in cellular hydration within 10 minutes of consuming Penta-hydrate™ micro-cluster water.

Decreased Lactic Acid Soreness from Exercise:

The inventors have received reports of reduced or eliminated soreness caused by lactic acid buildup during exercise as well as increased endurance and performance after consuming Penta-hydrate™ micro-cluster water. This includes elderly fibromyalgia patients. Penta-hydrate™ micro-cluster is thought to delay or prevent the on set of anaerobic cellular function by increasing cellular water and oxygen exchange keeping the cells operating aerobic condition for a longer time period during strenuous exercise, thus preventing or delaying the buildup of lactic acid in the body.

Increased Athletic Performance:

Test accomplished on three high performance athletes have demonstrated a marked increase in overall performance.

A 29 year old male Tri-athlete competing in the 1999 Coronado California $21^{st}$ annual Super Frog Half Iron Man Triathlon consumed (6) six 500 ml bottles of Penta-hydrate™ Micro-Cluster the day prior to the race and (6) six 500 ml bottles of Penta-hydrate™ during the race posted a finish time of 4:19:37 winning the overall male winner, finishing over 24 minutes ahead of the second place finisher in his age group and beating the combined time of the Navy SEAL Relay Team One's time of 4:26:09 which had a fresh man for each leg of the three events. Normally after such a demanding race this athlete would be extremely sore the next day, however drinking the Penta-hydrate™ Micro-Cluster Water he was not sore and competed in a 20 K cycle qualifier the following day. Subject Tri-Athlete has won numerous Triathlons' and qualified for the 1999 World-Championships in Australia.

A 39 year old male Tri-athlete competing in the San Diego Second Annual Duadrome World Championships on Aug. $8^{th}$ 1999 at the Morley Field Velodrome. Subject athlete was pre hydrated with Penta-hydrate™ Micro-Cluster Water set a new world record winning the 35–39 age group division, beating his own best time by 26 seconds in the male relay division and the course record by 3 seconds Both of the above Tri-athletes report dramatic increase in endurance and rapid recovery after strenuous exercise not experienced with conventional water and an ability to hydrate during the running portion of a triathlon, normally hydration is only accomplished during the cycling portion of a triathlon, due to normal water causing the subject to regurgitate, this problem is not encountered drinking Penta-hydrate™ Micro-Cluster Water due to its rapid absorption.

45-year-old woman TV 10 News anchor in San Diego, that also competes in rough ocean swimming. Consumed 500 ml of Penta-hydrate™ just prior to entering the water in a swim meet in Hawaii, won the gold medal in 45-year-old age division. Returned to San Diego and competed in the La Jolla rough water swim and won a gold medal. Next competed in the US Nationals held at Catalina Island in California and won the US National Gold Medal after drinking 500 ml of Penta-hydrate™ just prior to entering the water. She was not considered a contender for the Gold in the US Nationals.

Congestive Heart Failure:

The inventors have had several reports from subjects with congestive heart failure report ten minutes after consuming 500 ml of Penta-hydrate Pro™ their shortness of breath had gone away and their energy was increased.

Muscular Sclerosis MS:

A woman with Muscular Sclerosis was rushed to the hospital in San Antonio, Tex. having passed out from severe dehydration. The MS subject drank×500 ml bottles of Penta-hydrate™ their and was re-hydrated.

Colds, Flu, Sinus Infections and Energy:

58-year-old male with loss of spleen and 20-year sufferer of fibromyalgia, suffered from chronic sinus infections and annual bouts of the flu and reoccurring bouts of pneumonia.

He started drinking 6–500 ml bottles of Penta-hydrate™ Micro-Cluster Water per day 19 months ago. At that time he had a severe sinus infection that would have normally required antibiotics. While taking the Penta-hydrate™ Micro-Cluster Water, the sinus infection was cleared within three days and subject has not had a single sinus infection in 19 months. In addition he has not experienced any colds, flu or allergy conditions and is now for the first time in 20-years able to work with out fatigue.

Elimination of Edema:

In numerous test cases Penta-hydrate™ has eliminated edema in all test subjects from both chronic health conditions as well as surgically caused edema. In all cases edema was dramatically reduced after consuming as little as one 500 ml bottle of Penta-hydrate™ Micro-Cluster Water but no more than two 500 ml bottles were required. One such case was a middle-aged woman that had broken her forearm in two places. The forearm was in a cast and suffering severs edema, subject was given two 500 ml bottles of Penta-hydrate™ Micro-Cluster Water that she consumed from 3:00 pm until bedtime. Swelling was so bad that she could not insert a business card between her swollen arm and the cast. When she awoke at 7:00 am the next morning the swelling was reduced to where she was endanger of loosing the cast and had to return to the orthopedic surgeon to have the cast redone.

Liquid Nutritional Analyzer Results.

Liquid nutritional analyzer results utilizing a RJL Systems BIA101Q™ FDA registered analyzer for assessing cellular hydration and health. The following measurements were preformed on a 58 year-old male subject.

Time: 7:59 am October 9, 1999 Baseline Test:

Measured: Resistance: 413 ohms  Reactance: 53 ohms
Calculated: Impedance 416 ohms  Phase Angle: 7.3 degrees
Parallel Model: Resistance: 419.8 ohms  Capacitance: 973.0 pF

| Fluid Assessment: | Results: | Percent: | Normal Range: | Deviation: |
|---|---|---|---|---|
| Status: (Edema) | | | | |
| Total Body Water | 63.3 L | 52% (WT) | 40%–50% | +2 |
| Intracellular Water | 37.5 L | 59% (TBW) | 51%–60% | +0 |
| Extracellular Water | 25.8 L | 41% (TBW) | 39%–51% | +0 |
| Nutrition Assessment: | | | | |
| Basal Metabolism | 2069 Kcal | | | |
| Body Cell Mass | 90.6 lbs. | | 34% (WT) | |
| Fat Free Mass | 190.2 lbs. | | 71% | |
| Fat | 78.8 lbs. | | 29% | |
| ECT | 99.6 lbs. | | 52% | |
| Impedance Index | 1437 Normal | | | |

Time: 8:02 am consumed 500 ml Penta-hydrate Pro ™

Time: 8:12 am October 9, 1999
Measured: Resistance: 436 ohms  Reactance: 57 ohms
Calculated: Impedance 439.7 ohms  Phase Angle: 7.4 degrees
Parallel Model: Resistance: 443.5 ohms  Capacitance: 938.4 pF

| Fluid Assessment: | Results: | Percent: | Normal Range: | Deviation: |
|---|---|---|---|---|
| Status: (Edema) | | | | |
| Total Body Water | 63.3 L | 51% (WT) | 40%–50% | +1 |
| Intracellular Water | 37.1 L | 60% (TBW) | 51%–60% | +0 |
| Extracellular Water | 25.2 L | 40% (TBW) | 39%–51% | +0 |
| Nutrition Assessment: | | | | |
| Basal Metabolism | 2060 Kcal | | | |
| Body Cell Mass | 89.6 lbs. | | 33% (WT) | |
| Fat Free Mass | 188.0 lbs. | | 70% | |
| Fat | 81.0 lbs. | | 30% | |
| ECT | 99.6 lbs. | | 52% | |
| Impedance Index | 1469 Normal | | | |

Time: 8:38 am October 9, 1999
Measured: Resistance: 442 ohms  Reactance: 56 ohms
Calculated: Impedance 445.5 ohms  Phase Angle: 7.2 degrees
Parallel Model: Resistance: 449.1 ohms  Capacitance: 898.0 pF

| Fluid Assessment: | Results: | Percent: | Normal Range: | Deviation: |
|---|---|---|---|---|
| Status: (Edema) | | | | |
| Total Body Water | 62.0 L | 51% (WT) | 40%–50% | +1 |
| Intracellular Water | 36.6 L | 60% (TBW) | 51%–60% | +0 |
| Extracellular Water | 25.4 L | 40% (TBW) | 39%–51% | +0 |
| Nutrition Assessment: | | | | |
| Basal Metabolism | 2048 Kcal | | | |
| Body Cell Mass | 88.4 lbs. | | 33% (WT) | |
| Fat Free Mass | 187.5 lbs. | | 70% | |
| Fat | 81.5 lbs. | | 30% | |
| ECT | 99.1 lbs. | | 53% | |
| Impedance Index | 1426 Normal | | | |

Time: 8:43 am October 9, 1999
Measured: Resistance: 453 ohms  Reactance: 57 ohms
Calculated: Impedance 456.6 ohms  Phase Angle: 7.2 degrees
Parallel Model: Resistance: 460.2 ohms  Capacitance: 870.4 pF

| Fluid Assessment: | Results: | Percent: | Normal Range: | Deviation: |
|---|---|---|---|---|
| Status: (Edema) | | | | |
| Total Body Water | 63.6 L | 50% (WT) | 40%–50% | +0 |
| Intracellular Water | 36.2 L | 59% (TBW) | 51%–60% | +0 |
| Extracellular Water | 25.3 L | 41% (TBW) | 39%–51% | +0 |
| Nutrition Assessment: | | | | |
| Basal Metabolism | 2040 Kcal | | | |
| Body Cell Mass | 87.6 lbs. | | 33% (WT) | |
| Fat Free Mass | 186.5 lbs. | | 69% | |
| Fat | 82.5 lbs. | | 31% | |
| ECT | 99.0 lbs. | | 53% | |
| Impedance Index | 1421 Normal | | | |

Time: 8:45 Consumed additional 500 ml Penta-hydrate Pro ™

Time: 8:48 am October 9, 1999
Measured: Resistance: 431 ohms  Reactance: 60 ohms
Calculated: Impedance 435.2 ohms  Phase Angle: 7.9 degrees
Parallel Model: Resistance: 439.4 ohms  Capacitance: 1008.6 pF

| Fluid Assessment: | Results: | Percent: | Normal Range: | Deviation: |
|---|---|---|---|---|
| Status: (Edema) | | | | |
| Total Body Water | 62.5 L | 51% (WT) | 40%–50% | +1 |
| Intracellular Water | 37.9 L | 61% (TBW) | 51%–60% | +1 |
| Extracellular Water | 24.5 L | 39% (TBW) | 39%–51% | +0 |
| Nutrition Assessment: | | | | |
| Basal Metabolism | 2078 Kcal | | | |
| Body Cell Mass | 91.7 lbs. | | 34% (WT) | |
| Fat Free Mass | 188.4 lbs. | | 70% | |
| Fat | 80.6 lbs. | | 30% | |
| ECT | 96.8 lbs. | | 52% | |
| Impedance Index | 1561 Normal | | | |

Time: 9:07 am October 9, 1999
Measured: Resistance: 442 ohms  Reactance: 57 ohms
Calculated: Impedance 445.7 ohms  Phase Angle: 7.3 degrees
Parallel Model: Resistance: 449.4 ohms  Capacitance: 913.5 pF Fluid Assessment:  Results:  Percent:  Normal Range:  Deviation:

Status: (Edema)

-continued

| | | | |
|---|---|---|---|
| Total Body Water | 62.0 L | 51% (WT) | 40%–50% | +1 |
| Intracellular Water | 36.8 L | 59% (TBW) | 51%–60% | +0 |
| Extracellular Water | 25.2 L | 41% (TBW) | 39%–51% | +0 |

Nutrition Assessment:

| | | |
|---|---|---|
| Basal Metabolism | 2053 Kcal | |
| Body Cell Mass | 88.9 lbs. | 33% (WT) |
| Fat Free Mass | 187.5 lbs. | 70% |
| Fat | 81.5 lbs. | 30% |
| ECT | 98.6 lbs. | 53% |
| Impedance Index | 1452 Normal | |

Time: 9:27 am October 9, 1999
Measured: Resistance: 427 ohms           Reactance: 56 ohms
Calculated: Impedance 430.7 ohms         Phase Angle: 7.5 degrees
Parallel Model: Resistance: 434.3 ohms   Capacitance: 961.1 pF Fluid Assessment:   Results:   Percent:       Normal Range:   Deviation:

Status: (Edema)

| | | | | |
|---|---|---|---|---|
| Total Body Water | 62.7 L | 51% (WT) | 40%–50% | +1 |
| Intracellular Water | 37.4 L | 60% (TBW) | 51%–60% | +0 |
| Extracellular Water | 25.3 L | 40% (TBW) | 39%–51% | +0 |

Nutrition Assessment:

| | | |
|---|---|---|
| Basal Metabolism | 2066 Kcal | |
| Body Cell Mass | 90.3 lbs. | 34% (WT) |
| Fat Free Mass | 188.8 lbs. | 70% |
| Fat | 80.2 lbs. | 30% |
| ECT | 98.5 lbs. | 52% |
| Impedance Index | 1471 Normal | |

Time: 9:38 Consumed 500 ml Penta-hydrate ™

Time: 9:46 am October 9, 1999
Measured: Resistance: 430 ohms           Reactance: 59 ohms
Calculated: Impedance 434.0 ohms         Phase Angle: 7.8 degrees
Parallel Model: Resistance: 438.1 ohms   Capacitance: 996.9 pF Fluid Assessment:   Results:   Percent:       Normal Range:   Deviation:

Status: (Edema)

| | | | | |
|---|---|---|---|---|
| Total Body Water | 62.0 L | 51% (WT) | 40%–50% | +1 |
| Intracellular Water | 37.8 L | 60% (TBW) | 51%–60% | +0 |
| Extracellular Water | 24.7 L | 40% (TBW) | 39%–51% | +0 |

Nutrition Assessment:

| | | |
|---|---|---|
| Basal Metabolism | 2075 Kcal | |
| Body Cell Mass | 91.3 lbs. | 34% (WT) |
| Fat Free Mass | 188.5 lbs. | 70% |
| Fat | 80.5 lbs. | 30% |
| ECT | 97.2 lbs. | 52% |
| Impedance Index | 1539 Normal | |

Time: 10:32 am October 9, 1999
Measured: Resistance: 437 ohms           Reactance: 57 ohms
Calculated: Impedance 440.7 ohms         Phase Angle: 7.4 degrees
Parallel Model: Resistance: 444.4 ohms   Capacitance: 934.2 pF Fluid Assessment:   Results:   Percent:       Normal Range:   Deviation:

Status: (Edema)

| | | | | |
|---|---|---|---|---|
| Total Body Water | 62.2 L | 51% (WT) | 40%–50% | +1 |
| Intracellular Water | 37.0 L | 60% (TBW) | 51%–60% | +0 |
| Extracellular Water | 25.2 L | 40% (TBW) | 39%–51% | +0 |

Nutrition Assessment:

| | | |
|---|---|---|
| Basal Metabolism | 2058 Kcal | |
| Body Cell Mass | 89.5 lbs. | 33% (WT) |
| Fat Free Mass | 187.9 lbs. | 70% |
| Fat | 81.1 lbs. | 30% |
| ECT | 98.4 lbs. | 52% |
| Impedance Index | 1466 Normal | |

Although test subjects were well hydrated prior to testing, the results were dramatic. Analysis of the above tests clearly show rapid cellular fluid exchange not possible with current hydrating fluid hydrating technology, including intravenous hydration methods. Similar tests utilizing tap and purified water demonstrated no change in cellular fluid exchanges over the same time frames. Note even though over-hydration increased total body water, the intercellular and extracellular remained within normal range with rapid noted in and out exchanges seen in both intercellular and extracellular fluids. And a 1.0% decrease in edema is noted after consuming only 500 ml of Penta-hydrate™ micro-cluster water. It is worth noting that the base micro-cluster water without oxygen is even more dramatic, hydrating the cells in less time than the oxygenated version micro-cluster water. The overall change in the Impedance Index of 124 points is utilized by the RJA System as an overall indication of health. Changes of this magnitude are not seen in a 90 day period of monitoring in the absence of oxygenated micro-cluster water (Penta-hydrate™ Micro-Cluster Water). However, when Penta-hydrate™ Micro-Cluster Water was consumed the 124 point change occurred within a 2.5 hour period.

EXAMPLE 3

A novel water prepared by the method of the invention was characterized with respect to various parameters.

A. Conductivity

Conductivity was tested using the USP 645 procedure that specifies conductivity measurements as criteria for characterizing water. In addition to defining the test protocol, USP 645 sets performance standards for the conductivity measurement system, as well as validation and calibration requirements for the meter and conductivity. Conductivity testing was performed by West Coast Analytical Service, Inc. in Santa Fe Springs, Calif.

Conductility Test Results

| | RO water | Micro-cluster water | Micro-cluster water w/$O_2$ |
|---|---|---|---|
| Conductivity at 25° C.* ($\mu$mhos/cm) | 5.55 | 3.16 | 3.88 |

*Conductivity values are the average of two measurements.

The conductivity observed for the micro-cluster water is reduced by slightly more than half compared to the RO water. This is highly significant and indicates that the micro-cluster water exhibits significantly different behavior and is therefore substantively different, relative to RO unprocessed water.

B. Fourier Transform Infra Red Spectroscopy (FTIR)

Figure 5A:
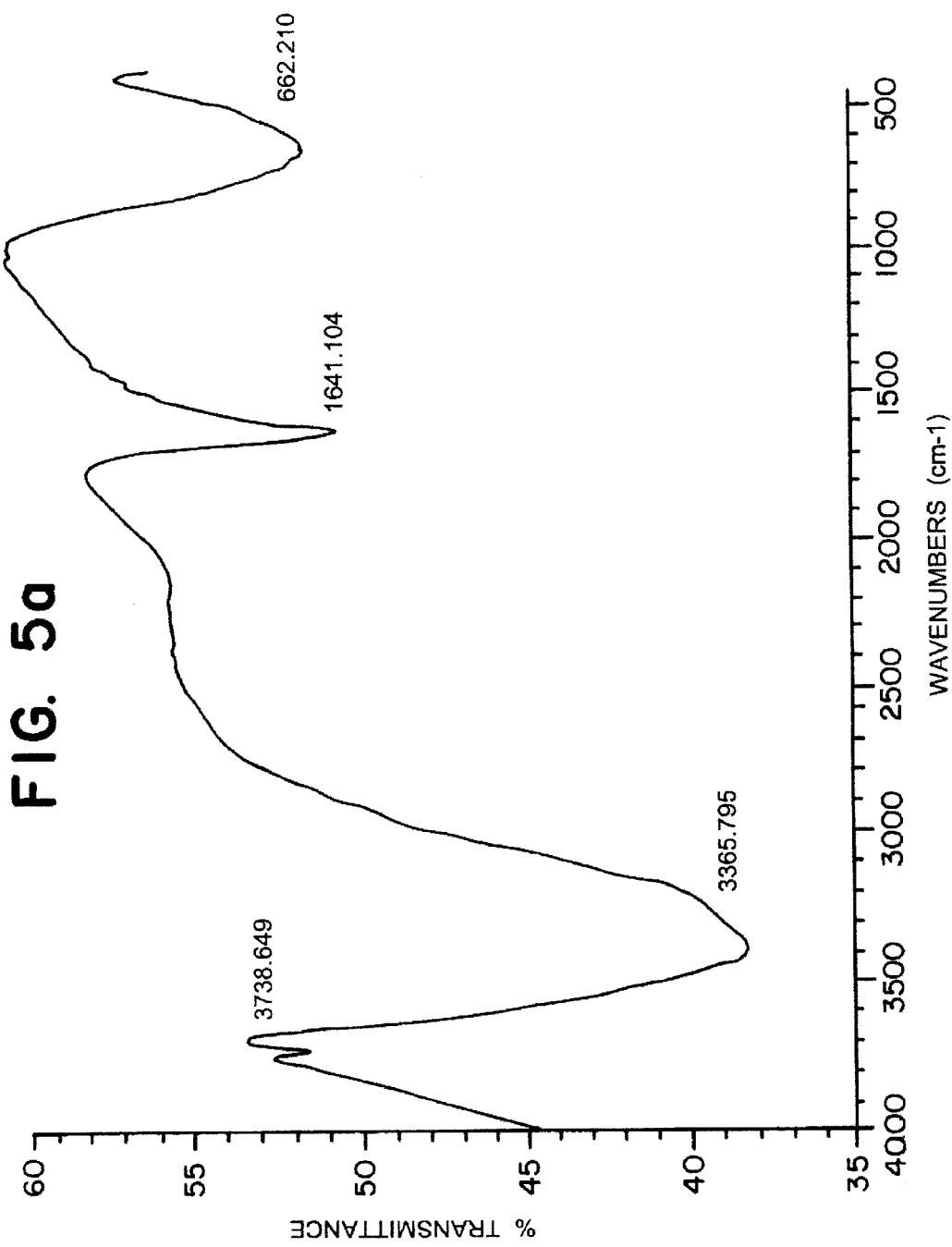
FIG. 5 shows FTIR spectra for RO water (FIG. 5(a)) and processed micro-cluster water (FIG. 5(b)).

Water, a strong absorber in the IR spectral region, has been well-characterized by FTIR and shows a major spectral line at approximately 3000 wave numbers corresponding to O—H bond vibrations. This spectral line is characteristic of the hydrogen bonding structure in the sample. An unprocessed RO water sample, Sample A, and a unoxygenated micro-cluster water sample, Sample B, were each placed between silver chloride plates, and the film of each liquid analyzed by FTIR at 25° C. The FTIR tests were performed by West Coast Analytical Service, Inc. in Santa Fe Springs, Calif. using a Nicolet Impact 400D™ benchtop FTIR. The FTIR spectra are shown in FIG. 5.

In comparing the FTIR spectra for the unoxygenated micro-cluster and RO waters, it is clear that the two samples have a number of features in common, but also significant differences. A major sharp feature at approximately 2650 wave numbers in the FTIR spectrum is observed for the micro-cluster water (FIG. 5(b)). The RO water has no such feature (FIG. 5(a)). This indicates that the bonds in the water sample are behaving differently and that their energetic interaction has changed. These results suggest that the unoxygenated micro-cluster water is physically and chemically different than RO unprocessed water.

C. Simulated Distillation

Simulated distillations were carried out on RO water and unoxygenated micro-cluster water without oxygenation by West Coast Analytical Service, Inc. in Santa Fe Springs, Calif.

Simulated Distillation Test Results

|  | RO Water | Unoxygenated Micro-cluster water |
|---|---|---|
| Boiling Point range* (deg. C.) | 98–100 | 93.2–100 |

*Corrected for barometric pressure.

These results show a significant lowering of the boiling temperature of the lowest boiling fraction in the unoxygenated micro-cluster water sample. The lowest boiling fraction for micro-cluster water is observed at 93.2° C. compared with a temperature of 98° C. for the lowest boiling fraction of RO water. This suggests that the process has significantly changed the compositional make-up of molecular species present in the sample. Note that lower boiling species are typically smaller, which is consistent with all observed data and the formation of micro-clusters.

D. Thermogravimetric Analysis

In this test, one drop of water was placed in a dsc sample pan and sealed with a cover in which a pin-hole was precision laser-drilled. The sample was subject to a temperature ramp increase of 5 degrees every 5 minutes until the final temperature. TGA profiles were run on both unoxygenated micro-cluster water and RO water for comparison.

Figure 6:
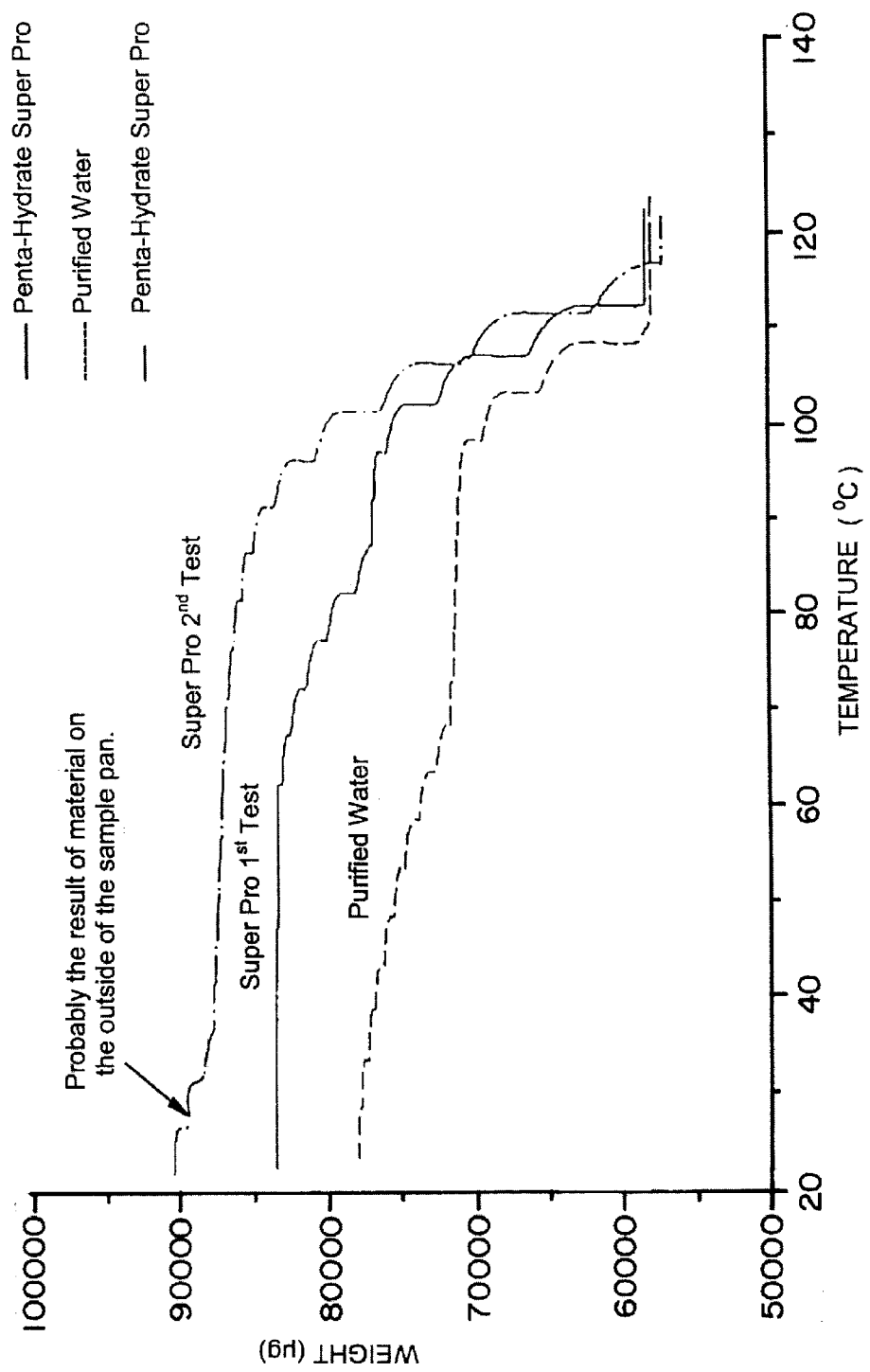
FIG. 6 shows TGA plots for RO water and oxygenated micro-cluster water.

The TGA analysis was performed on a TA Instruments Model TFA2950™ by Analytical Products in La Canada, Calif. The TGA test results are shown in FIG. 6. Three test runs utilizing three different samples are shown. The RO water sample is designated, "Purified Water" on the TGA plot. The unoxygenated micro-cluster water was run in duplicate, designated Super Pro $1^{st}$ test and Super Pro $2^{nd}$ Test. The unoxygenated micro-cluster water and the unprocessed RO water showed significantly greater weight loss dynamics. It is evident that the RO water began losing mass almost immediately, beginning at about 40° C. until the end temperature. The micro-cluster water did not begin to lose mass until about 70° C. This suggests that the processed water has a greater vapor pressure between 40 and 70° C. compared to unprocessed RO water. The TGA results demonstrated that the vapor pressure of the unxoygenated micro-cluster water was lower when the boiling temperature was reached. These data once again show that the unoxygenated micro-cluster water is significantly changed compared to RO water. These data once again show that the unoxygenated micro-cluster water also shows more features between the temperatures of 75 and 100+deg. C. These features could account for the low boiling fraction(s) observed in the simulated distillation.

E. Nuclear Magnetic Resonance (NMR) Spectroscopy

Figure 7C:
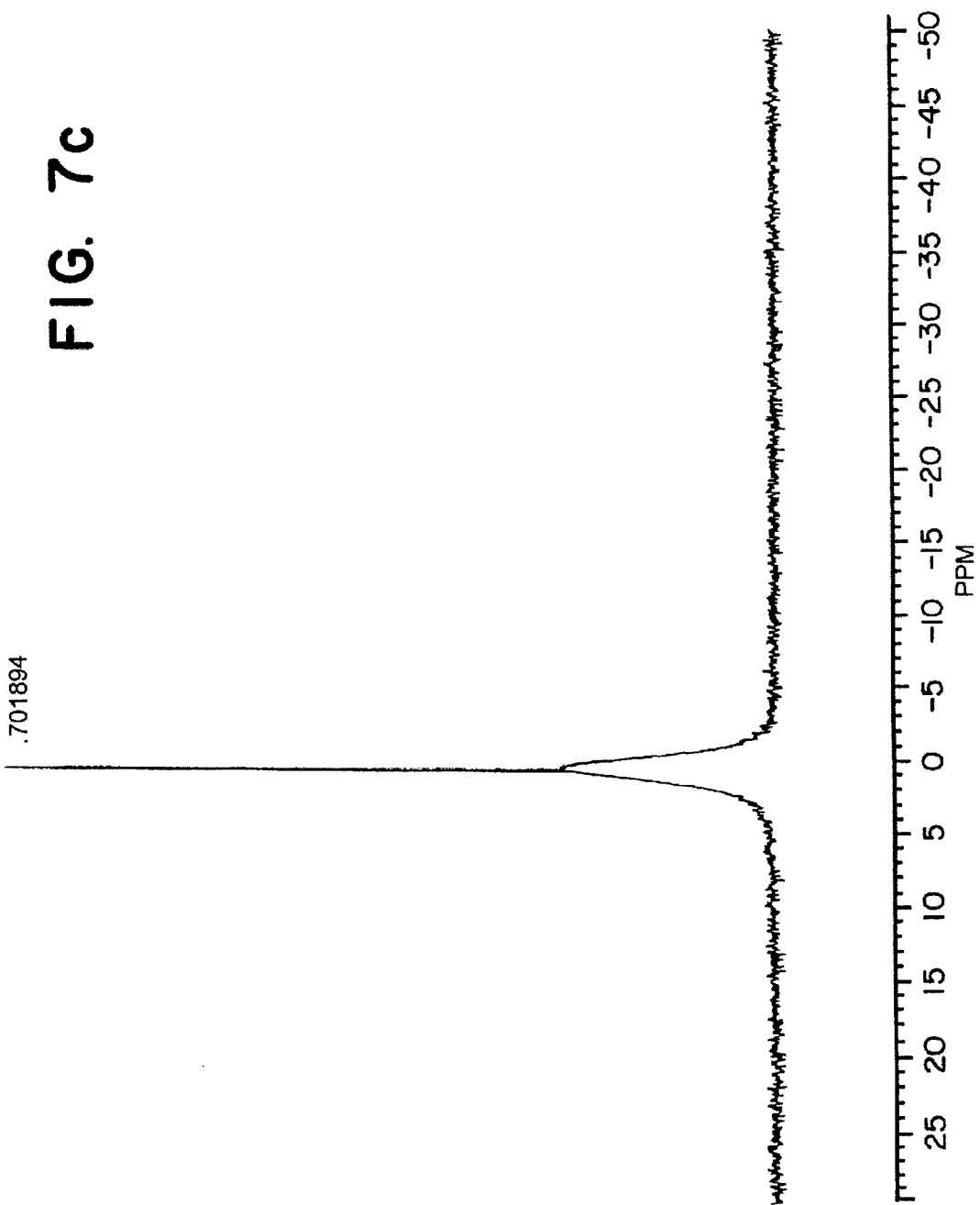
FIG. 7 shows NMR spectra for RO water (FIG. 7(a)), micro-cluster water without oxygenation (FIG. 7(b)) and micro-cluster water with oxygenation (FIG. 7(c)).

NMR testing was performed by Expert Chemical Analysis, Inc. in San Diego, Calif. utilizing a 600 MHz Bruker AM500™ instrument. NMR studies were performed on micro-cluster water with and without oxygen and on RO water. The results of these studies are shown in FIG. 7. In $^{17}$O NMR testing a single expected peak was observed for RO water (FIG. 7 (a)). For micro-cluster water without oxygen (FIG. 7(b)), the single peak observed was shifted +54.1 Hertz relative to the RO water, and for the micro-cluster water with oxygen (FIG. 7(c)), the single peak was shifted +49.8 Hertz relative to the RO water. The shifts of the observed NMR peaks for the micro-cluster water and RO water. Also of significance in the NMR data is the broadening of the peak observed with the micro-cluster water sample compared to the narrower peak of the unprocessed sample.

What is claimed is:

1. A process for producing a micro-cluster liquid, comprising:
   subjecting a liquid to cavitation such that dissolved entrained gases in the liquid form a plurality of cavitation bubbles; and
   subjecting the liquid containing the plurality of cavitation bubbles to a reduced pressure, wherein the reduction in pressure causes breakage of large liquid molecule matrices into smaller liquid molecule matrices, thereby producing a micro-cluster liquid.

2. The process of claim 1, wherein the liquid is substantially free of minerals.

3. The process of claim 1, wherein the liquid is water.

4. The process of claim 3, wherein the water is substantially free of minerals.

5. The process of claim 4, wherein the process is repeated until the water reaches about 140° F. (about 60° C.).

6. The process of claim 1, wherein the cavitation is provided by subjecting the liquid to a first pressure followed by a rapid depressurization to a second pressure to form cavitation bubbles.

7. The process of claim 6, wherein the pressurization is provided by a pump.

8. The process of claim 6, wherein the first pressure is about 55 psig to more than about 120 psig.

9. The process of claim 6, wherein the second pressure is about atmospheric pressure.

10. The process of claim 1, wherein the pressure change causes the plurality of cavitation bubbles to implode or explode.

11. The process of claim 10, wherein the pressure change creates a plasma which dissociates the local atoms and reforms the atoms at a different bond angle and strength.

12. The process of claim 1, further comprising cooling the liquid to a temperature ranging from about 4° C. to about 15° C.

13. The process of claim 1, further comprising providing gas to the micro-cluster liquid.

14. The process of claim 13, wherein the gas is oxygen.

15. The process of claim 14, wherein the oxygen is provided for about 5 to about 15 minutes.

16. A process for producing a micro-cluster liquid, comprising:
   subjecting a liquid to a pressure sufficient to pressurize the liquid;

emitting the pressurized liquid such that a continuous stream of liquid is created;

subjecting the continuous stream of liquid to a multiple rotational vortex having a partial vacuum pressure such that dissolved entrained gases in the liquid form a plurality of cavitation bubbles; and subjecting the liquid containing the plurality of cavitation bubbles to a reduced pressure, wherein the plurality of cavitation bubbles implode or explode causing shock waves that break large liquid molecule matrices into smaller liquid molecule matrices, thereby producing a micro-cluster liquid.

17. The process of claim 16, wherein the liquid is substantially free of minerals.

18. The process of claim 16, wherein the liquid is water.

19. The process of claim 18, wherein the water is substantially free of minerals.

20. The process of claim 19, wherein the process is repeated until the water reaches about 140° F. (about 60° C.).

21. The process of claim 16, wherein the cavitation is provided by subjecting the liquid to a first pressure followed by a rapid depressurization to a second pressure to form cavitation bubbles.

22. The process of claim 21, wherein the pressurization is provided by a pump.

23. The process of claim 21, wherein the first pressure is about 55 psig to more than 120 psig.

24. The process of claim 21, wherein the second pressure is about atmospheric pressure.

25. The process of claim 21, wherein the second pressure is less than 5 psig.

26. The process of claim 16, wherein the pressure change causes the plurality of cavitation bubbles to implode or explode.

27. The process of claim 26, wherein the pressure change creates a plasma which dissociates the local atoms and reforms the atoms at a different bond angle and strength.

28. The process of claim 16, further comprising cooling the liquid to a temperature ranging from about 4° C. to about 15° C.

29. The process of claim 16, further comprising providing gas to the micro-cluster liquid.

30. The process of claim 29, wherein the gas is oxygen.

31. The process of claim 30, wherein the oxygen is provided for about 5 to about 15 minutes.

32. The process of claim 31, wherein the pressure is from about 15 to 20 psig.

33. A micro-cluster liquid produced by the process of claim 1 or 16.

34. Micro-cluster water produced by the process of claim 1 or 16.

35. An article of manufacture, comprising the micro-cluster liquid of claim 33.

36. The article of manufacture of claim 35, wherein the liquid is water.

37. An article of manufacture, comprising the micro-cluster water of claim 34.

38. The article of manufacture of claim 37, wherein the article of manufacture is bottled micro-cluster water.

39. A composition consisting essentially of a micro-cluster water having a conductivity of about 3.0 to 4.0 μmhos/cm, and oxygen.

40. A composition consisting essentially of a micro-cluster water having a Fourier transform infrared (FTIR) spectrophotometric pattern comprising a major sharp feature at about 2650 wave numbers, and oxygen.

41. A composition consisting essentially of a micro-cluster water having a vapor pressure between about 40° C. and 70° C. as determined by thermogravimetric analysis, and oxygen.

42. A composition consisting essentially of a micro-cluster water having an $^{17}O$ NMR peak shift of at least about +30 Hertz relative to reverse osmosis water, and oxygen.

43. The composition of claim 42, wherein the peak shift is at least about +40 Hertz relative to reverse osmosis water, and oxygen.

44. A method for modulating a cellular performance comprising contacting a cell with a micro-cluster water made by the process of claim 1 or claim 16.

45. The method of claim 44, wherein the modulated cellular performance comprises lowering free radical levels in the cell.

46. A method for lowering free radical levels in a cell comprising contacting the cell with a micro-cluster water made by the process of claim 1 or claim 16.

47. A method for removing stains from fabrics comprising contacting the fabric with a micro-cluster water made by the process of claim 1 or claim 16.

48. A composition comprising a micro-cluster water having a conductivity of about 3.0 to 4.0 μmhos/cm, and oxygen, said composition being substantially free of minerals.

49. The composition of claim 48, further comprising a nutritional agent or a medication.

50. An article of manufacture, comprising the composition of claim 48 or 49.

51. A method for modulating a cellular performance comprising contacting a cell with a composition of any one of claims 39 to 43.

52. A method for lowering free radical levels in a cell comprising contacting the cell with a composition of any one of claims 39 to 43.

53. A method for removing stains from fabrics comprising contacting the fabric with a composition of any one of claims 39 to 43.

* * * * *